United States Patent [19]  [11] 3,951,980
Henry et al.  [45] Apr. 20, 1976

[54] 3-SUBSTITUTED-8-METHYL-3,8-DIAZABICYCLO[3.2.1]OCTANES

[75] Inventors: David W. Henry, Menlo Park; Priscilla A. Sturm, Mountain View, both of Calif.

[73] Assignee: Stanford Research Institute, Menlo Park, Calif.

[22] Filed: Aug. 21, 1975

[21] Appl. No.: 606,338

Related U.S. Application Data

[62] Division of Ser. No. 468,370, May 9, 1974, Pat. No. 3,905,979.

[52] U.S. Cl. ............................ 260/268 BF; 424/250
[51] Int. Cl.$^2$............... C07D 451/02; C07D 487/08
[58] Field of Search ............................ 260/268 BF

[56] References Cited
UNITED STATES PATENTS
3,905,979  9/1975  Henry et al. .................. 260/268 BF OTHER PUBLICATIONS
Giorgio Cignarella et al., Journal of Medicinal Chemistry, Vol. 6, pp. 385–387, (1963).

*Primary Examiner*—Alton D. Rollins
*Assistant Examiner*—Jose Tovar
*Attorney, Agent, or Firm*—Donovan J. De Witt

[57] ABSTRACT

Twelve analogs of diethylcarbamazine as prepared by acylation of 3- and 8-methyl-3,8-diazabicyclo[3.2.1]octane, 2-methyl-2,5-diazabicyclo[2.2.2]octane, and 2-methyl-2,5-diazabicyclo[2.2.1]heptane with diethylcarbamyl chloride, ethyl chloroformate, ethyl isocyanate, and cyclohexanecarbonyl chloride. These compounds are formally derived from diethylcarbamazine in possessing two- or one-carbon bridges over the piperazine ring. The compounds have utility as antifilarial agents and as bronchodilators.

5 Claims, No Drawings

3-SUBSTITUTED-8-METHYL-3,8-DIAZABICYCLO[3.2.1]OCTANES

ORIGIN OF INVENTION

The invention described herein was made in the course of work under a grant or award from the Department of Health, Education and Welfare.

This is a division of application Ser. No. 468,370, filed May 9, 1974 now U.S. Pat. No. 3,905,979.

SUMMARY OF INVENTION

This invention relates to the provision of 12 analogs of diethycarbamazine, said compounds having one or another of the structural formulae given below, where the roman numeral presents in connection with each R substituent group refers to the corresponding example in which the preparation of the indicated compound is described:

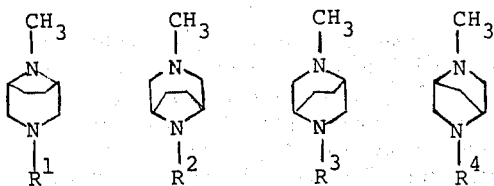

wherein $R^1$ represents —$CON(C_2H_5)_2$ (I), —$COOC_2H_5$ (II), —$CONHC_2H_5$ (III), or

$R^2$ represents —$CON(C_2H_5)_2$ (V), —$COOC_2H_5$ (VI), or —$CONHC_2H_5$ (VII); $R^3$ represents —$CON(C_2H_5)_2$ (VIII), —$COOC_2H_5$ (IX), or —$CONHC_2H_5$ (X); and $R^4$ represents —$CON(C_2H_5)_2$ (XI) or —$COOC_2H_5$ (XII).

Also included within the scope of the invention are pharmaceutically acceptable salts of these compounds, the salts being acid addition salts and water soluble.

The foregoing compounds can be designated as follows:
  I. 3-Diethylcarbamyl-8-methyl-3,8-diazabicyclo[3.2.1]octane.
  II. 3-Carbethoxy-8-methyl-3,8-diazabicyclo[3.2.1]octane.
  III. 3-(N-Ethylcarbamyl)-8-methyl-3,8-diazabicyclo[3.2.1]octane.
  IV. 3-Cyclohexanecarbonyl-8-methyl-3,8-diazabicyclo[3.2.1]octane.
  V. 8-(N,N-Diethylcarbamyl)-3-methyl-3,8-diazabicyclo[3.2.1]octane.
  VI. 8-Carbethoxy-3-methyl-3,8-diazabicyclo[3.2.1]octane.
  VII. 8-(N-Ethylcarbamyl)-3-methyl-3,8-diazabicyclo[3.2.1]octane.
  VIII. 2-(N,N-Diethylcarbamyl)-5-methyl-2,5-diazabicyclo[2.2.2]octane.
  IX. 2-Carbethoxy-5-methyl-2,5-diazabicyclo[2.2.2]octane.
  X. 2-(N-Ethylcarbamyl)-5-methyl-2,5-diazabicyclo[2.2.2]octane.
  XI. 2-(N,N-Diethylcarbamyl)-5-methyl-2,5-diazabicyclo[2.2.1]heptane.
  XII. 2-Carbethoxy-5-methyl-2,5-diazabicyclo[2.2.1]heptane.

A method for preparing each of the foregoing compounds is presented in the following examples:

EXAMPLE 1

3-Diethylcarbamyl-8-methyl-3,8-diazabicyclo[3.2.1]octane

The captioned compound was prepared using the method and precursor compounds as follows:
Diethyl cis-1-methylpyrrolidine-2,5-dicarboxylate.

To liquid methylamine (3.5 g, 0.113 mole), collected in the chilled glass liner of a 500-ml stainless steel bomb, was added a solution of 12.0 g (0.0334 mole) diethyl meso-α,α'-dibromoadipate, prepared according to the procedure of P. C. Guha and D. K. Sankaran in "Organic Syntheses", Collective Volume III, p 623, 1955, published by Wiley, New York, N.Y.; in benzene (40 ml). The sealed bomb was then heated at 90°C overnight. After cooling, the bomb was opened, the white solid methylamine hydrobromide was collected and the filtrate evaporated in vacuo to a yellow oil. Fractionation through a Vigreux column yielded the product, 4.6 g (61%) boiling point 73°–76°C (0.2 mm).

An elemental analysis gave these results: Analysis — calculated for $C_{11}H_{19}NO_4$ (percent): C, 57.6; H, 8.35; N, 6.11. Found (percent): C, 57.0; H, 8.39; N, 6.29.
Ethyl cis-5-(N-benzylcarbamyl)-1-methylpyrrolidine-2-carboxylate.

A solution of diethyl cis-1-methylpyrrolidine-2,5-dicarboxylate (10.95 g, 0.0478 mole) and benzylamine (5.2 ml, 0.048 mole) in 30 ml xylene was refluxed 72 hours at 140°C. After evaporation of the xylene in vacuo, the oily residue was fractionated on a Vigreux column. After an initial fraction of the starting compound (0.49 g), the product was collected: 7.11 g (boiling point 160°C, 0.25 mm).

An elemental analysis gave these results: Analysis — calculated for $C_{16}H_{22}N_2O_3$ (percent): C, 66.2; H, 7.64; N, 9.65. Found (percent): C, 65.9; H, 7.43; N, 9.85.
3-Benzyl-8-methyl-3,8-diazabicyclo[3.2.1]octane-2,3-dione.

Ethyl cis-5-(N-benzylcarbamyl)-1-methyl pyrrolidine-2-carboxylate (59.0 g, 0.203 mole) in 622 ml 1N sodium hydroxide (in 75% aqueous ethanol) was stirred at room temperature for 30 minutes. The reaction was neutralized with dry hydrogen chloride to a phenolphthalein endpoint, and the white solid (sodium chloride) was collected by filtration. The filtrate was evaporated in vacuo, redissolved in absolute ethanol, and reevaporated to a foamy glass. This crude intermediate, cis-5-(N-benzylcarbamyl)-1-methyl-pyrrolidine-2-carboxylic acid, was heated in acetic anhydride (565 ml) at 110°C for 2 hours. The cooled, dark amber reaction mixture was filtered to remove precipitated inorganic salts (22 g). The filtrate was evaporated in vacuo to leave a dark brown crystalline solid (52.7 g). Recrystallization from chloroform-diethyl ether gave 38 g of brown solid, melting point 92°–95°C. Filtration of this in chloroform solution through 400 g of alumina afforded, after removal of solvent, 32.8 g (66%) of colorless product, melting point 98°–102°C, which was suitable for subsequent reactions. An earlier reaction provided the analytical sample, melting point 105.5°–108°C.

An elemental analysis gave these results: Analysis — calculated for $C_{14}H_{16}N_2O_2$ (percent): C, 68.8; H, 6.60; N, 11.5. Found (percent): C, 69.0; H, 6.71; N, 11.4.

3-Benzyl-8-methyl-3,8-diazabicyclo[3.2.1]octane.

A solution of 3-benzyl-8-methyl-3,8-diazabicyclo[3.2.1]octane-2,4-dione (32.8 g, 0.135 mole) in dioxane (500 ml) was rapidly added dropwise to a suspension of lithium aluminum hydride (20.5 g, 0.54 mole) in dioxane (500 ml). The reaction was refluxed 18 hours, cooled, and worked up by slow and careful dropwise addition of water with stirring until the grey suspension turned white. The mixture was filtered, the inorganic salts washed with dioxane and the combined filtrate and washing evaporated in vacuo to leave a pale yellow oil (24.9 g). Chromatography on 370 g of alumina in chloroform provided 17.7 g of pure oily free base. Treatment of the free base dissolved in diethyl ether with three equivalents of anhydrous ethanolic hydrogen chloride gave 19.1 g (41%) of the dihydrochloride salt which analyzed as the monohydrate after drying in vacuo (0.2 mm) at 100°C for 18 hours. It melted at approximately 110°C, resolidified and remelted at 210°–219°C.

An elemental analysis gave these results: Analysis — calculated for $C_{14}H_{20}N_2 \cdot 2HCl \cdot H_2O$ (percent): C, 54.7; H, 7.87; N, 9.12. Found (percent): C, 54.6, H, 7.84; N, 9.05.

8-Methyl-3,8-diazabicyclo[3.2.1]octane.

A mixture of 3-benzyl-8-methyl-3,8-diazabicyclo[3.2.1]octane dihydrochloride monohydrate (18.1 g, 0.059 mole) in absolute ethanol (200 ml) and 10% palladium on charcoal (3.0 g) was hydrogenated for 2 hours at atmospheric pressure. Sufficient water was added to dissolve the insoluble hydrochloride salt that had formed, and the reaction was filtered. The filtrate was evaporated in vacuo, the residue was triturated in hot absolute ethanol, and the mixture was filtered to yield 8.98 g of 8-methyl-3,8-diazabicyclo[3.2.1]octane dihydrochloride, melting point 315°C (dec.). The mother liquor was treated with ethanolic dry hydrogen chloride to afford an additional 2.28 g. Yield: 12.26 g (96%).

An elemental analysis gave the following results: Analysis — calculated for $C_7H_{14}N_2 \cdot 2HCl$ (percent): C, 42.2; H, 8.10; N, 14.1. Found (percent): C, 42.4; H, 7.98; N, 14.1

3-(N,N-Diethylcarbamyl)-8-methyl-3,8-diazabicyclo[3.2.1]octane.

8-Methyl-3,8-diazabicyclo[3.2.1]octane dihydrochloride (2.5 g, 0.0126 mole) was stirred vigorously in a 2-phase system of 20 ml aqueous 10% sodium hydroxide and 50 ml chloroform for one-half hour at room temperature. Then at 0°C, 2.56 g (0.0189 mole) diethylcarbamyl chloride was added and the reaction was stirred 18 hours at room temperature. Hot water (50 ml) was added. The solution was extracted twice with chloroform and the extract dried with sodium sulfate. After evaporation, a solution of the oily free base in diethyl ether was treated with ethanolic hydrogen chloride to yield 2.92 g (89% yield) 3-(N,N-diethylcarbamyl)-8-methyl-3,8-diazabicyclo[3.2.1]octane monohydrochloride, a white solid melting at 202°–205°C.

An elemental analysis gave the following results: Analysis — calculated for $C_{12}H_{23}N_3O \cdot HCl$ (percent): C, 55.1; H, 9.24; N, 16.1. Found (percent): C, 55.3; H, 9.37; N, 16.1.

EXAMPLE 2

3-Carbethoxy-8-methyl-3,8-diazabicyclo[3.2.1]octane

The captioned compound was prepared as follows:

8-Methyl-3,8-diazabicyclo[3.2.1]octane dihydrochloride (2.5 g, 0.0126 mole), prepared as described in Example 1, was reacted with 1.51 ml (0.0189 mole) ethyl chloroformate according to the procedure described above for 3-(N,N-diethylcarbamyl)-8-methyl-3,8-diazabicyclo[3.2.1]octane in Example 1. A white monohydrochloride, melting point 200°–205°C, was obtained in 73% yield: 2.16 g.

An elemental analysis gave the following results: Analysis — calculated for $C_{10}H_{18}N_2O_2 \cdot HCl$ (percent): C, 51.2; H, 8.16; N, 11.9. Found (percent): C, 51.2; H, 8.03; N, 11.9.

EXAMPLE 3

3-(N-Ethylcarbamyl)-8-methyl-3,8-diazabicyclo[3.2.1]octane

The captioned compound was prepared as follows:

8-Methyl-3,8-diazabicyclo[3.2.1]octane dihydrochloride (2.5 g, 0.0126 mole), prepared as described in Example 1, was reacted with 2.0 ml (0.0253 mole) ethyl isocyanate according to the procedure described above for 3-(N,N-diethylcarbamyl)-8-methyl-3,8-diazabicyclo[3.2.1]octane in Example 1. A white monohydrochloride, melting point 246°–250°C (dec.) was obtained in 79% yield: 2.33 g.

An elemental analysis gave the following results: Analysis — calculated for $C_{10}H_{19}N_3O \cdot HCl$ (percent): C, 51.4; H, 8.62; N, 18.0. Found (percent): C, 51.5; H, 8.59; N, 18.0.

EXAMPLE 4

3-Cyclohexanecarbonyl-8-methyl-3,8-diazabicyclo[3.2.1]octane

The captioned compound was prepared as follows:

Cyclohexane carboxylic acid (1.29 g, 0.010 mole) and 1.2 g (0.010 mole) thionyl chloride were heated in a dry atmosphere at 90°C for 1 hour. To this cyclohexane carboxylic acid chloride, at 0°C, was added a mixture of 2.0 g (0.010 mole) 8-methyl-3,8-diazabicyclo[3.2.1]octane dihydrochloride (prepared as described in Example 1), 1.6 g sodium hydroxide dissolved in 16 ml water, and 16 ml chloroform which had been stirred vigorously at room temperature and then chilled to 0°C. The reaction was stirred at 0°C for 1 hour. The crude product was isolated as a yellow oil by extraction of the aqueous phase with chloroform. Purification by chromatography on alumina followed by treatment with ethanolic hydrogen chloride yielded 1.58 g (58% yield) of the desired product as a white monohydrochloride, melting point 263°–268°C.

an elemental analysis gave the following results: Analysis — calculated for $C_{14}H_{24}N_2O \cdot HCl$ (percent): C, 61.6; H, 9.24; N, 10.3. Found (percent): C, 61.8; H, 9.22; N, 10.4

EXAMPLE 5

8-(N,N-Diethylcarbamyl)-3-methyl-3,8-diazabicyclo[3.2.1]octane

The captioned compound was prepared as follows:
Cis-N-benzylpyrrolidine-2,5-dicarboxylic acid.

The first step in the preparation of this compound was to prepare diethyl cis-N-benzylpyrrolidine-2,5- dicarboxylate from diethyl meso-α,α'-dibromoadipate (see Example 1) as described by G. Cignarella and G. Nathansohn in J. Org. Chem., 26, p 1500, 1961. Diethyl cis-N-benzylpyrrolidine-2,5-dicarboxylate (103.5 g, 0.340 mole) was then heated in 1 liter concentrated hydrochloric acid at 100°C for 2 hours. Upon cooling, a crystalline solid precipitated. It was isolated by filtration, triturated with acetone-diethyl ether, and recrystallized from ethanol-water to give 41.3 g (49%) of partially hydrated product, melting point 254°-258°C. An infrared spectrum analysis gave $\lambda_{max}.^{Nujol} = 2.95$ μ (O—H).

An elemental analysis gave the following results: Analysis — calculated for $C_{13}H_{15}NO_4.0.33 H_2O$ (percent): C, 61.3; H, 6.18; N, 5.49. Found (percent): C, 61.6; H, 6.30; N, 5.56.

The anhydrous product failed to produce the subsequent cyclic anhydride when submitted to the same conditions as the hydrated form.

Cis-5-(N-methylcarbamyl)-1-benzylpyrrolidine-2-carboxylic acid.

Cis-N-benzylpyrrolidine-2,5-dicarboxylic acid (41.3 g, 0.166 mole) and acetic anhydride (206.5 ml) were heated carefully together to 100°C; the solid gradually dissolved, and the mixture assumed a dark brown color. In typical experiments, solution was complete in 10–30 minutes, depending on the state of subdivision of the starting material. Heating time was minimized. Just before the last solid dissolved, the excess acetic anhydride was removed in vacuo, and the brown oily residue of crude cis-N-benzylpyrrolidine-2,5-dicarboxylic acid anhydride was taken up in 400 ml benzene. Anhydrous methylamine (0.33 mole as 9.9% solution in benzene) was added in two portions, and the mixture was heated on the steam bath for 45 minutes. After cooling, the crude cis-5-(N-methylcarbamyl)-1-benzylpyrrolidine-2-carboxylic acid (35.8 g) was collected by filtration, washed with benzene and recrystallized from ethanol. Yield: 31.4 g (72%), melting point 190°-192°C.

An elemental analysis gave the following results: Analysis — calculated for $C_{14}H_{18}N_2O_3$ (percent): C, 64.1; H, 6.92; N, 10.7. Found (percent): C, 64.0; H, 6.91; N, 10.4.

8-Benzyl-3-methyl-3,8-diazabicyclo[3.2.1]octane-2,4-dione

Cis-5-(N-methylcarbamyl)-1-benzylpyrrolidine-2-carboxylic acid (32.3 g, 0.123 mole) and acetic anhydride (160 ml) were heated together at 100°C for 45 minutes after all of the solid had dissolved. Removal of solvent in vacuo left a red-brown oil that was dissolved in a minimum amount of benzene. After removal of 2.0 g of unreacted cis-5-(N-methylcarbamyl)-1-benzylpyrrolidine-2-carboxylic acid by filtration, the solution of desired product was chromatographed on 900 g alumina with benzene elution to give 13.2 g (44%) of pure, oily 8-benzyl-3-methyl-3,8-diazabicyclo[3.2.1]octane-2,4-dione. Treatment of a sample with excess ethanolic hydrogen chloride in diethyl ether solution produced a hydrochloride salt, melting point 140°-170°C. A sample of the free base, melting point 73°-75°C, was subsequently obtained by slow crystallization from benzene.

An elemental analysis of the hydrochloride salt gave the following results: Analysis — Calculated for $C_{14}H_{16}N_2O_2.HCl$ (percent): C, 59.9, H, 6.10, N, 9.98. Found (percent): C, 59.7; H, 6.17; N, 9.82.

8-Benzyl-3-methyl-3,8-diazabicyclo[3.2.1]octane.

Reduction of 9.6 g (0.039 mole) of 8-benzyl-3-methyl-3,8-diazabicyclo[3.2.1]octane-2,4-dione with lithium aluminum hydride in tetrahydrofuran by the procedure used for the preparation of 3-benzyl-8-methyl-3,8-diazabicyclo[3.2.1]octane, as described in Example 1, gave 8.3 g of crude desired product. Chromatography on 124 g alumina with chloroform elution gave 6.9 g (81%) of pure, oil 8-benzyl-3-methyl-3,8-diazabicyclo[3.2.1]octane. The hydrochloride salt, formed in diethyl ether by addition of three equivalents of ethanolic hydrogen chloride, melted at 263.5°-272°C (dec.) with sublimation above 180°C.

An elemental analysis gave the following results: Analysis — calculated for $C_{14}H_{20}N_2.2HCl$ (percent): C, 58.1; H, 7.66; N, 9.68. Found (percent): C, 58.0; H, 7.72; N, 9.74.

The free base 8-benzyl-3-methyl-3,8-diazabicyclo[3.2.1]octane is a known compound having been prepared by G. Cignarella and G. Nathansohn as related in J. Org. Chem., 26, p 1500, 1961.

3-Methyl-3,8-diazabicyclo[3.2.1]octane.

A solution of 8.2 g (0.038 mole) 8-benzyl-3-methyl-3,8-diazabicyclo[3.2.1]octane in 80 ml absolute ethanol containing 0.11 mole dry hydrogen chloride was hydrogenated in the presence of 1.5 g 10% palladium on charcoal at ambient temperature and pressure for 20 hours. The precipitated hydrochloride salt of the desired product was dissolved by addition of a little water, and, after filtration, the solvent was removed carefully in vacuo. The crystalline residue (6.9 g) was triturated with ethanol-diethyl ether containing dry hydrogen chloride to insure complete formation of the somewhat unstable dihydrochloride salt. Filtration gave 6.0 g (79%) of pure product, melting point 272°-280°C (dec.) with sublimation above 200°C.

An elemental analysis gave the following results: Analysis — calculated for $C_7H_{14}N_2.2HCl$ (percent): C, 42.2; H, 8.10; N, 14.1. Found (percent): C, 42.1; H, 8.29, N, 13.8.

The free base 3-methyl-3,8-diazabicyclo[3.2.1]octane is a known compound having been prepared by G. Cignarella and G. Nathansohn as related in J. Org. Chem., 26, p 1500, 1961.

8-(N,N-Diethylcarbamyl)-3-methyl-3,8-diazabicyclo[3.2.1]octane.

A solution of 1.17 g (0.0093 mole) of 3-methyl-3,8 diazabicyclo[3.2.1]Octane (free base) in 15 ml tertiary butanol was treated with 1.94 ml (0.014 mole) triethylamine and 1.9 g (0.014 mole) diethylcarbamyl chloride. The mixture was stirred at ambient temperature for 4 hours. Hot water (30 ml) was added and stirring was continued for 30 minutes; extraction with chloroform followed by drying of the combined extracts with sodium sulfate and thorough removal of volatiles in vacuo gave 1.86 g of crude product. This was dissolved in diethyl ether and treated with one equivalent of maleic acid dissolved in minimum absolute ethanol. The colorless precipitate of 8-(N,N-Diethylcarbamyl)-3-methyl-3,8-diazabicyclo[3.2.1]octane maleate (2.58 g, 82%) was collected by filtration.

An elemental analysis gave the following results: Analysis — calculated for $C_{12}H_{23}N_3O.C_4H_4O_4$ (percent): C, 56.3; H, 7.97; N, 12.3. Found (percent): C, 56.4; H, 8.04; N, 12.4.

EXAMPLE 6

8-Carbethoxy-3-methyl-3,8-diazabicyclo[3.2.1]octane

The captioned compound was prepared as follows:

A two phase mixture of 3.0 g (0.0151 mole) 3-methyl-3,8-diazabicyclo[3.2.1]octane dihydrochloride, prepared as described in Example 5, in 50 ml CHCl$_3$ and 25 ml of 10% aqueous sodium hydroxide was stirred vigorously for one-half hour at room temperature. Then, at 0°C, 1.8 ml (0.0227 mole) ethyl chloroformate was added. The reaction was stirred at room temperature for 18 hours. The two phases were separated; the aqueous phase was extracted with chloroform and the combined extracts were washed with water followed by evaporation to dryness. An hydrochloride salt was made by treating a solution of the pale yellow oil in diethyl ether with ethanolic hydrogen chloride and filtering to collect 3.22 g (91% yield) white solid with melting point 209°–210°C.

An elemental analysis gave the following results:
Analysis — calculated for C$_{10}$H$_{18}$N$_2$O$_2$.HCl (percent): C, 51.2; H, 8.16; N, 11.9. Found (percent): C, 51.3; H, 8.28; N, 12.0.

EXAMPLE 7

8-(N-Ethylcarbamyl)-3-methyl-3,8-diazabicyclo[3.2.1]octane

The captioned compound was prepared as follows:
3-Methyl-3,8-diazabicyclo[3.2.1]octane dihydrochloride (3.0 g, 0.0151 mole), prepared as described in Example 5, was reacted with 1.21 ml (0.0151 mole) ethyl isocyanate in a procedure as described for 8-carbethoxy-3-methyl-3,8-diazabicyclo[3.2.1]octane in Example 6. The crude desired product, as the free base, was purified by chromatography on alumina with chloroform elution. An hydrochloride salt was made by treatment of a solution of the free base in diethyl ether with ethanolic hydrogen chloride and filtering to collect 1.0 g (28% yield) white solid exhibiting a dual melting point of 100°–140°C and 191°–202°C until dried 2 hours at 126°C in vacuo after which the desired product hydrochloride salt melted at 205°–215°C.

An elemental analysis gave the following results:
Analysis — calculated for C$_{10}$H$_{19}$N$_3$O.HCl (percent): C, 51.4; H, 8.64; N, 18.0. Found (percent): C, 51.2; H, 8.90; N, 18.0.

EXAMPLE 8

2-(N,N-Diethylcarbamyl)-5-methyl-2,5-diazabicyclo[2.2.2]octane

The captioned compound was prepared as follows:
Diethyl 2,5-diphthalimidoadipate.

Diethyl 2,5-diphthalimidoadipate was prepared according to a modification of the procedure used by Merck and Co. for the preparation of dimethyl-2,5-diphthalimidoadipate as described in their Netherlands Patent Application 6400946, 1964; Chem. Abstr., 62, 7761d, 1965.

To a cold (0°C) solution of phthalmide (9.7 g, 0.0666 mole) dried at 85°C for 2 hours in dry dimethylformamide (40 ml) was added 2.85 g of 56.4% sodium hydride in mineral oil followed by a solution of 10.0 g (0.028 mole) diethyl meso-$\alpha$,$\alpha'$-dibromoadipate; prepared as described by P. C. Guha and D. K. Sankaran in "Organic Syntheses", Collective Volume III, p 623, 1955, published by Wiley, New York, N.Y.; in 70 ml dry dimethylformamide. The reaction was heated at 80°C for 1 hour, cooled, and filtered to remove a small amount of white solid. Mineral oil was removed by pentane extraction, and the dimethylformamide was removed in vacuo. The residue was taken up in chloroform and extracted successively with water, 0.1N sodium hydroxide, and water. Removal of solvent in vacuo left an oil that crystallized on cooling. Trituration with diethyl ether left 4.5 g (33%) of product, melting point 133°–136° C.

An elemental analysis gave the following results:
Analysis — calculated for C$_{26}$H$_{24}$N$_2$O$_8$ (percent): C, 63.4; H, 4.91; N, 5.69. Found (percent): C, 63.4; H, 4.75; N, 5.95.

Dimethyl 2,5-diaminoadipate.

Diethyl 2,5-diphthalimidoadipate was converted to 2,5-diaminoadipic acid according to the procedure described in the Merck and Co. Netherlands Patent Application 6400946, 1964; Chem. Abstrs., 62, 7761d, 1965, in which dimethyl 2,5-diphthalimidoadipate was used as the starting material.

2,5-Diaminoadipic acid was then converted to dimethyl 2,5-diaminoadipate as described in the Merck patent which had recorded a melting point of 201°–203°C for the hydrochloride salt, as opposed to a melting point of 230°–240°C (dec.) recorded by the authors of this patent.

An elemental analysis gave the following results:
Analysis — calculated for C$_8$H$_{16}$N$_2$O$_4$.2HCl (percent): C, 34.7; H, 6.55; N, 10.11. Found (percent): C, 34.2; H, 6.52; N, 9.86.

2,5-Diazabicyclo[2.2.2]octane-3,6-dione.

The procedure used in the preparation of 2,5-diazabicyclo[2.2.2]octane-3,6-dione was a modification of the method utilized by Merck and Co. in their Netherlands Patent Application 6400946, 1964; Chem. Abstr., 62, 7761d, 1965. Dimethyl 2,5-diaminoadipate dihydrochloride (60.0 g, 0.217 mole) was combined with sodium methoxide (25.8 g, 0.478 mole) in 6 liters n-butanol and refluxed 5 days at which time the infrared spectrum of an evaporated aliquot indicated completion. The bulk of the n-butanol was removed by distillation and the remainder by evaporation in vacuo. The still wet tan solid was triturated in hot ethanol and chilled, and the mixture was centrifuged. The solid (49.0 g), a mixture of sodium chloride and desired product, was sublimed at 210°–220°C and 0.3 mm; the collected material was then triturated in hot chloroform, cooled, and filtered to yield 17.0 g 2,5-diazabicyclo[2.2.2]octane-3,6-dione, melting point 275°–277°C. The supernatant was evaporated in vacuo and dissolved in chloroform, and, after several days, an additional 1.3 g of product was collected for an overall yield of 18.3 g (58%).

The Merck patent had recorded a melting point of 272°–273°C.

2,5-Dibenzyl-2,5-diazabicyclo[2.2.2]octane-3,6-dione.

A hot solution of 36.6 g (0.262 mole) of 2,5-diazabicyclo[2.2.2]octane-3,6-dione in 800 ml dry dimethylformamide was added rapidly from a dropping funnel to 12.5 g (0.52 mole) of oil-free sodium hydride. After stirring for 1 hour, the mixture was chilled and treated with 67.5 ml (0.59 mole) benzyl chloride during a period of a few minutes. After stirring at room temperature for 18 hours, 1 liter of water was added cautiously, and the mixture was extracted with chloroform. The extracts were washed with water, dried with sodium sulfate, and evaporated to dryness to yield a crystalline residue. Trituration in diethyl ether provided 77.0 g (91%) of product as colorless needles, melting point 168°–170°C.

An elemental analysis gave the following results: Analysis — calculated for $C_{20}H_{20}N_2O_2$ (percent): C, 75.0; H, 6.29; N, 8.74. Found (percent): C, 74.8; H, 6.37; N, 8.61.

2,5-Dibenzyl-2,5-diazabicyclo[2.2.2]octane.

Reduction of 6.1 g (0.019 mole) of 2,5-dibenzyl-2,5-diazabicyclo[2.2.2]octane-3,6-dione by the procedure employed to prepare 8-benzyl-3-methyl-3,8-diazabicyclo[3.2.1]octane as related under Example 5 gave 4.9 g (88%) of 2,5-dibenzyl-2,5-diazabicyclo[2.2.2]octane as a colorless oil.

An elemental analysis gave the following results: Analysis — calculated for $C_{20}H_{24}N_2$ (percent): C, 82.2; H, 8.27; N, 9.58. Found (percent): C, 82.4; H, 8.53; N, 9.64.

2,5-Diazabicyclo[2.2.2]octane.

Catalytic debenzylation of 2,5-dibenzyl-2,5-diazabicyclo[2.2.2]octane (8.00 g, 0.0274 mole) under conditions used to prepare 3-methyl-3,8-diazabicyclo[3.2.1]octane as related in Example 5, produced 4.15 g (82%) of pure 2,5-diazabicyclo[2.2.2]octane dihydrochloride after trituration of the crude with anhydrous methanol. It decomposed slowly from 300°C, without melting, to 360°C. Merck and Co. Netherlands Patent Application 6400946, 1964; Chem. Abstr., 62, 7761d, 1965, had prepared this compound by another synthetic route and had recorded a melting point of 335°C. (dec.).

An elemental analysis gave the following results: Analysis — calculated for $C_6H_{12}N_2.2HCl$ (percent): C, 38.9; H, 7.62; N, 15.1. Found (percent): C, 38.7; H, 7.47; H, 14.9.

2-Benzoyl-2,5-diazabicyclo[2.2.2]octane.

This compound was prepared as described by Merck and Co. in their Netherlands Patent Application 6400946, 1964; Chem. Abstr., 62, 7761d, 1965. Optimum recovery of the desired product required a highly baxic medium and repeated chloroform extraction. Final purification was achieved by chromatography on alumina with chloroform elution. A melting point of 119°–121°C was recorded in contrast to a melting point of 109°–111°C recorded by the Merck patent.

An elemental analysis on the hydrochloride salt of 2-benzoyl-2,5-diazabicyclo[2.2.2]octane gave the following results:

Analysis — calculated for $C_{13}H_{16}N_2O.HCl$ (percent): C, 61.8; H, 6.78; N, 11.1. Found (percent): C, 61.5; H, 6.92, N, 10.9.

2-Benzoyl-5-methyl-2,5-diazabicyclo[2.2.2]octane.

To 7.4 ml of 88% formic acid (0.17 mole) was added 14.6 g (0.0675 mole) of 2-benzoyl-2,5-diazabicyclo[2.2.2]octane with stirring at 0°C. A 36% aqueous solution of formaldehyde (6.0 ml, 0.078 mole) was added, and, after visible gas evolution had ceased, the mixture was heated at 80°C until renewed gas evolution has stopped 91 hour). After 3 hours at 90°–100° C, volatiles were removed in vacuo. The residue was dissolved in water, made alkaline with 20% aqueous sodium hydroxide, and extracted with chloroform. After drying with sodium sulfate, the extracts yielded 15.6 g (100%) of colorless oily 2-benzoyl-5-methyl-2,5-diazabicyclo[2.2.2]octane that was homogeneous by thin layer chromatography. It was characterized as the oxalate salt, melting point 167°–169°(dec.).

An elemental analysis gave the following results: Analysis — calculated for $C_{14}H_{18}N_2O.H_2C_2O_4$ (percent): C, 60.0; H, 6.29; N, 8.74. Found (percent): C, 59.8; H, 6.26; N, 8.87.

2-Methyl-2,5-diazabicyclo[2.2.2]octane.

A solution of 2-benzoyl-5-methyl-2,5-diazabicyclo[2.2.2]octane (17.2 g, 0.074 mole) in concentrated hydrochloric acid (172 ml) was refluxed 48 hours. The solution was evaporated to dryness in vacuo and the residue triturated with diethyl ether. The supernatant, after centrifugation, was decanted, and the procedure was repeated using absolute ethanol. The hygroscopic residue of 2-methyl-2,5-diazabicyclo[2.2.2]octane.2HCl (12.1 g, 81.5%) was dried in vacuo. It slowly decomposed above 300°C.

An elemental analysis gave the following results: Analysis — calculated for $C_7H_{14}N_2.2HCl$ (percent): C, 42.2; H, 8.10, N, 14.1. Found (percent): C, 42.0; H, 8.21; N, 13.8.

2-(N,N-Diethylcarbamyl)-5-methyl-2,5-diazabicyclo[2.2.2]octane.

A mixture of 2.5 g (0.0126 mole) 2-methyl-2,5-diazabicyclo[2.2.2]octane dihydrochloride, 20 ml of 10% aqueous sodium hydroxide and 50 ml chloroform were stirred vigorously for one-half hour at room temperature. Then, at 0° C, 2.56 g (0.189 mole) diethylcarbamyl chloride was added and the reaction was stirred at room temperature for 18 hours. Thereafter, the two phases were separated and the aqueous phase was extracted with chloroform. The combined extracts were dried over sodium sulfate and evaporated to dryness to yield 2.9 g (100%) yellow oil. This crude free base failed to yield either crystalline hydrochloride or maleic acid salts. It was therefore chromatographed on acid-washed alumina with first diethyl ether elution and then chloroform elution. The recovered free base in diethyl ether solution when treated with 2 equivalents of ethanolic hydrogen chloride yielded 2.24 g (60%) 2-(N,N-diethylcarbamyl)-5-methyl-2,5-diazabicyclo[2.2.2]octane dihydrochloride, melting point 144°–157° C. This salt was moderately hygroscopic and slowly lost hydrogen chloride.

An elemental analysis gave the following results: Analysis — calculated for $C_{12}H_{23}N_3O.2HCl$ (percent): C, 48.3; H, 8.45; N, 14.1. Found (percent): C, 48.1; H, 8.65; N, 14.2.

EXAMPLE 9

2-Carbethoxy-5-methyl-2,5-diazabicyclo[2.2.2]octane

The captioned compound was prepared as follows:

2-Methyl-2,5-diazabicyclo[2.2.2]octane dihydrochloride, prepared as described in Example 8, (2.5 g, 0.0126 mole) was reacted with 1.5 ml (0.016 mole) ethyl chloroformate according to the procedure described for 2-(N,N-diethylcarbamyl)-5-methyl-2,5-diazabicyclo[2.2.2]octane dihydrochloride in Example 8. Filtration of the crude free base as a solution in chloroform through a pad of acid-washed alumina gave a material which formed 1.7 g of a crystalline hydrochloride salt when treated with ethanolic hydrogen chloride. The salt was moderately hygroscopic and melted at 149°–155° C.

An elemental analysis gave the following results: Analysis — calculated for $C_{10}H_{18}N_2O_2.HCl$ (percent): C, 51.2; H, 8.16; N, 11.9. Found (percent): C, 51.3; H, 8.36; N, 11.9.

EXAMPLE 10

2-(N-Ethylcarbamyl)-5-methyl-2,5-diazabicyclo[2.2.2]octane

The captioned compound was prepared as follows:

2-Methyl-2,5-diazabicyclo[2.2.2]octane dihydrochloride prepared as described in Example 8 (2.5 g, 0.0126 mole) was reacted with 1.5 ml (0.0189 mole) ethyl isocyanate according to the procedure described for 2-(N,N-diethylcarbamyl)-5-methyl-2,5-diazabicyclo[2.2.2]octane dihydrochloride in Example 8. The crude oily product (1.65 g — 65%) in diethyl ether solution was treated with ethanolic hydrogen chloride to afford 1.55 g (52%) of a crystalline white hydrochloride salt, melting point 220°–228° C (dec.).

An elemental analysis gave the following results: Analysis — calculated for $C_{10}H_{19}N_3O.HCl$ (percent): C, 51.39; H, 8.62; N, 17.98. Found (percent): C, 51.62; H, 8.83; N, 18.09.

EXAMPLE 11

2-(N,N-Diethylcarbamyl)-5-methyl-2,5-diazabicyclo[2.2.2]heptane

The captioned compound was prepared as follows: N-Tosylhydroxy-L-prolinol.

A solution of 182.6 g (0.642 mole) N-tosylhydroxy-L-proline, made according to the procedure of P. S. Portoghese and A. A. Mikhail as reported in J. Org. Chem., 31, p 1059, 1966, in 800 ml dry THF was added over a 3 hour period to 1300 ml of 0.5 m diborane in tetrahydrofuran with stirring at 0° C. The reaction mixture solidified into a white opaque gel. This was broken up by hand, 800 ml of tetrahydrofuran was added, and the mixture was refluxed 2.5 hours with mechanical stirring. During this time, most of the solid redissolved. After 18 hours at ambient temperature, the reaction mixture was chilled, and 6N hydrochloric acid was carefully added until gas evolution ceased. One liter of water was added, and the homogeneous solution was diluted with chloroform until two phases formed. The aqueous phase was separated and extracted with additional chloroform. The combined organic phases were washed with water, dried with sodium sulfate, and evaporated in vacuo to leave a semi-solid residue (159.6 g) that gave 80.0 g (50.5%, melting point 130°–132° C), of N-tosylhydroxy-L-prolinol upon crystallization from ethyl acetate. Portoghese and Mikkail reported a melting point of 131°–133° C for the same compound made via the methyl ester of N-tosylhydroxy-L-lproline.

2-Benzyl-5-(N,N-diethylcarbamyl)-2,5-diazabicyclo[2.2.1]heptane.

N-Tosylhydroxy-L-prolinol was converted to 2-tosyl-5-benzyl-2,5-diazabicyclo[2.2.1]heptane which in turn was cyclized to N-benzyl-2,5-diazabicyclo[2.2.1]heptane dihydriodide all according to the procedures reported by P. S. Portoghese and A. A. Mikhail in J. Org. Chem., 31, p 1059, 1966. A two-phase mixture of 6.0 g (0.0135 mole) 2-benzyl-2,5-diazabicyclo[2.2.1]heptane dihydroiodide, 27 ml 20% aqueous sodium hydroxide, and 50 ml chloroform was stirred 1 hour at 0° C. Diethylcarbamyl chloride (2.75 g, 0.0202 mole) in 5 ml chloroform was added and the mixture stirred at 0° C for 1 hour. After 68 hours at ambient temperature, 50 ml hot water was added, and 30 minutes later the organic phase was isolated. One chloroform extract of the aqueous phase was combined with the original organic phase, and the solution was dried with sodium sulfate. Evaporation to dryness in vacuo left 4.87 g of oily crude product that was chromatographed on alumina with chloroform elution. The purified product in 100 ml diethyl ether was converted to the salt by addition of dry 5.9M ethanolic hydrogen chloride. The tacky precipitate was triturated with diethyl ether-acetone to give pure 2-benzyl-5-(N,N-diethyl-carbamyl)2,5-diazabicyclo[2.2.1]heptane hydrochloride (3.2 g, 80% yield, melting point 147°–149° C).

An elemental analysis gave the following results: Analysis — calculated for $C_{17}H_{25}N_3O.HCl$ (percent): C, 63.0; H, 8.09; N, 13.0. Found (percent): C, 63.0; H, 7.94; N, 13.0.

2-(N,N-Diethylcarbamyl)-5-methyl-2,5-diazabicyclo[2.2.1]heptane.

2-Benzyl-5-(N,N-diethylcarbamyl)-2,5-diazabicyclo[2.2.1]heptane hydrochloride (3.2 g, 0.0099 mole) in 50 ml 95% ethanol was hydrogenated at ambient temperature and pressure in the presence of 0.5 g 10% palladium on charcoal. When the debenzylation was complete after 2 hours, the mixture was filtered, and volatiles were removed in vacuo. Diethyl ether was added to the residue followed by ethanolic 5.9M hydrogen chloride until further additions induced no more cloudiness. Chilling at 0° C effected crystallization of the oily precipitate of 2-(N,N-Diethylcarbamyl)-2,5-diazabicyclo[2.2.1]heptane hydrochloride. Upon isolation by filtration, this proved to be very hygroscopic, and the oily free base was regenerated by chloroform extraction of an alkaline solution of the salt. The free base (1.85 g) was mixed at 0° C with 1.02 ml 88% formic acid (0.024 mole) and 0.80 ml 33% aqueous formaldehyde (0.01 mole) and heated 30 minutes on the steam bath until gas evolution ceased. After heating a further 18 hours at 90° C, the reaction mixture was chilled, made basic with 20% sodium hydroxide and extracted with chloroform. Evaporation of the extract left 1.3 g (66%) of oily product that was homogeneous by thin layer chromatography on alumina with chloroform. The maleic acid salt was obtained from diethyl ether solution by addition of 0.605 g of maleic acid dissolved in a small volume of ethanol. The slightly hygroscopic salt was recrystallized from acetone-diethyl ether to afford 1.24 g (40%) of pure 2-(N,N-Diethylcarbamyl)-5-methyl-2,5-diazabicyclo[2.2.1]heptane maleate, melting point 82°–84° C.

An elemental analysis gave the following analysis: Analysis — calculated for $C_{11}H_{21}N_3O.C_4H_4O_4$ (percent): C, 55.0; H, 7.70; N, 12.8. Found (percent): C, 55.0; H, 7.45; N, 12.6.

EXAMPLE 12

2-Carbethoxy-5-methyl-2,5-diazabicyclo[2.2.1]heptane

The captioned compound was prepared as follows: 2-Benzyl-5-carbethoxy-2,5-diazabicyclo[2.2.1]heptane.

Using the procedure for preparation of 2-benzyl-5-(N,N-diethylcarbamyl)-2,5-diazabicyclo[2.2.1]heptane hydrochloride as related in Example 11, 29.0 g of 2-benzyl-2,5-diazabicyclo[2.2.1]heptane dihydroiodide, prepared according to the procedure given in Example 11, was treated with 1.5 equivalents of ethyl chloroformate to yield crude product. Dry column chromatography, a technique described by B. Loev and M. M. Goodman in Chem. Ind. (London), p 2026, 1967, on 1700 g alumina using chloroform development provided 11.6 g (68%) of pure product, characterized as the maleate salt, melting point 124°–128° C.

An elemental analysis gave the following results: Analysis — calculated for $C_{15}H_{20}N_2O_2 \cdot C_4H_4O_4$ (percent): C, 60.6; H, 6.43; N, 7.44. Found (percent): C, 60.6; H, 6.57; N, 7.56.

2-Benzyl-5-methyl-2,5-diazabicyclo[2.2.1]heptane.

A solution of 11.6 g (0.045 mole) of 2-benzyl-5-carbethoxy-2,5-diazabicyclo[2.2.1]heptane in 400 ml dry tetrahydrofuran was added dropwise rapidly to a stirred suspension of 6.77 g (0.178 mole) lithium aluminum hydride in 100 ml dry tetrahydrofuran at 0° C. The mixture was refluxed 18 hours, cooled, and cautiously treated with water to decompose excess lithium aluminum hydride. The mixture was filtered, and the solvents were removed in vacuo. The oily residue (6.5 g) was dissolved in diethyl ether, and the solution was filtered and treated with 11 ml of 5.9M ethanolic hydrogen chloride. The precipitate was collected and partitioned between diethyl ether and water; the aqueous phase was made basic with 40% aqueous sodium hydroxide and extracted with diethyl ether. The combined extracts were dried with sodium sulfate and evaporated to leave 4.78 g of oily product that was homogeneous by thin layer chromatography on alumina developed with chloroform. This was reconverted to the dihydrochloride salt (6.03 g, 47.5% yield, melting point 80°–200° C dec.).

An elemental analysis gave the following results: Analysis — calculated for $C_{13}H_{18}N_2 \cdot 2HCl \cdot 0.5H_2O$ (percent): C, 54.9; H, 7.45; N, 9.86. Found (percent): C, 54.9; H, 7.42; N, 9.96.

2-Methyl-2,5-diazabicyclo[2.2.1]heptane.

Catalytic hydrogenolysis of 6.03 g (0.0219 mole) of 2-benzyl-5-methyl-2,5-diazabicyclo[2.2.1]heptane dihydrochloride hemihydrate in 95% ethanol using 0.90 g 10% palladium on charcoal at atmospheric pressure was complete in 0.5 hours. Filtration, followed by evaporation of the solvent and trituration of the residue with absolute ethanol, gave 2.0 g light yellow solid product, melting point 264° C (dec.). Drying at 100° C at 1 mm for 18 hours removed persistent water of hydration. An additional 1.3 g of 2-methyl-2,5-diazabicyclo[2.2.1] was obtained by treating the ethanol supernatant with additional ethanolic hydrogen chloride. Total yield: 3.3 g (81.5%).

An elemental analysis gave the following results: Analysis — calculated for $C_6H_{12}N_2 \cdot 2HCl$ (percent): C, 38.9; H, 7.62; N, 15.1. Found (percent): C, 38.7; H, 7.80; N, 15.1.

2-Carbethoxy-5-methyl-2,5-diazabicyclo[2.2.1]heptane.

2-Methyl-2,5-diazabicyclo[2.2.1]heptane dihydrochloride (3.3 g, 0.0178 mole) was stirred with 35 ml each of 10% aqueous sodium hydroxide and chloroform at 0° C for one-half hour. Ethyl chloroformate (2.56 ml, 0.0267 mole) was added and the reaction stirred at room temperature for 1½ hours. The 2 phases were separated and the aqueous layer was extracted once with chloroform. The combined chloroform extracts were washed with water, dried with sodium sulfate and evaporated to dryness to yield 3.34 g oil homogeneous on thin-layer chromatography on alumina developed with chloroform. A solution of the oil in absolute ehtanol was combined with an equivalent of maleic acid dissolved in ethanol and treated with diethyl ether to incipient turbidity. A moderately hygroscopic maleic acid salt was isolated in 75% yield with melting point 78°–82° C.

An elemental analysis gave the following results: Analysis — calculated for $C_9H_{16}N_2O_2 \cdot C_4H_4O_4$ (percent): C, 52.0; H, 6.71; N, 9.33. Found (percent): C, 52.2; H, 6.75; N, 9.45.

When evaluated against Litomosoides carinii in the gerbil all the compounds hereof strongly suppressed blood microfilaremia levels but did not affect the adult worms. Several compounds were nearly equivalent to diethylcarbamazine in activity.

The compounds of the present invention also have utility as bronchodilators. This was determined by orally dosing guinea pigs with one or another of the compounds, and then placing the pigs in a closed chamber for exposure to an aerosol spray containing histamine diphosphate solution. Observations were made as to the time elapsing to prostration of the pigs in this environment. The periods so recorded were significantly longer than those observed for the control animals which received no dosage of the chemicals.

The compounds of the present invention have been described in the examples in the form of acid addition salts, such salts being water soluble and therefore of somewhat greater utility than the compounds would be without the inclusion of the acid component. In preparing the compounds as salts, any pharmaceutically acceptable acid material may be employed, e.g., hydrochloride acid, sulfuric acid, citric acid, or acetic acid, for example. The pure compounds can be prepared in non-salt form by treating the salt with alkali in aqueous solution, the compound being extracted from the aqueous reaction system with a solvent such as diethyl ether or chloroform. The evaporation of the solvent then leaves the compound, usually in the form of an oil.

What is claimed is:

1. A compound having the structure

wherein $R^1$ represents $-CON(C_2H_5)_2$, $-COOC_2H_5$, $-CONHC_2H_5$, or

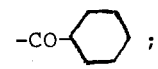

together with the acid addition salts of said compounds.

2. The compound of claim 1 which is 3-diethylcarbamyl-8-methyl-3,8-diazabicyclo[3.2.1]octane; together with the acid addition salts of said compound.

3. The compound of claim 1 which is 3-carbethoxy-8-methyl-3,8-diazabicyclo[3.2.1]octane; together with the acid addition salts of said compound.

4. The compound of claim 1 which is 3-(N-ethylcarbamyl)-8-methyl-3,8-diazabicyclo[3.2.1]octane; together with the acid addition salts of said compound.

5. The compound of claim 1 which is 3-cyclohexanecarbonyl-8-methyl-3,8-diazabicyclo[3.2.1]octane; together with the acid addition salts of said compound.

* * * * *